(12) United States Patent
Purdham et al.

(10) Patent No.: US 9,799,191 B2
(45) Date of Patent: Oct. 24, 2017

(54) ELECTRICAL PLUG DEVICE FOR MONITORING PERSONAL ACTIVITY

(71) Applicant: 3Rings Care Ltd., Oxford (GB)

(72) Inventors: Stephen Purdham, Oxford (GB); Gareth Reakes, Oxford (GB)

(73) Assignee: 3Rings Care Ltd, Oxfordshire (GB)

( * ) Notice: Subject to any disclaimer, the term of this patent is extended or adjusted under 35 U.S.C. 154(b) by 0 days.

(21) Appl. No.: 15/323,375

(22) PCT Filed: Jul. 7, 2015

(86) PCT No.: PCT/EP2015/065510
§ 371 (c)(1),
(2) Date: Dec. 30, 2016

(87) PCT Pub. No.: WO2016/005399
PCT Pub. Date: Jan. 14, 2016

(65) Prior Publication Data
US 2017/0140628 A1 May 18, 2017

(30) Foreign Application Priority Data
Jul. 8, 2014 (GB) .................................. 1412148.7

(51) Int. Cl.
G08B 1/08 (2006.01)
G08B 21/04 (2006.01)
G08B 21/02 (2006.01)

(52) U.S. Cl.
CPC ..... *G08B 21/0407* (2013.01); *G08B 21/0283* (2013.01); *G08B 21/0484* (2013.01)

(58) Field of Classification Search
CPC .................................................. G08B 21/0407
(Continued)

(56) References Cited

U.S. PATENT DOCUMENTS 7,064,670 B2 * 6/2006 Galperin ............ G08B 13/2462
340/539.11
8,320,649 B2 * 11/2012 Shahaf ............... G06K 9/00543
382/128

(Continued)

FOREIGN PATENT DOCUMENTS

EP 2264680 A1 12/2010
EP 2804162 A2 11/2014

(Continued)

OTHER PUBLICATIONS

International Preliminary Report on Patentability for International Application No. PCT/EP2015/065510, dated Jan. 10, 2017, 8 pgs.

(Continued)

Primary Examiner — Santiago Garcia
(74) Attorney, Agent, or Firm — Hunter Clark PLLC

(57) ABSTRACT

A method of operating a server for remotely monitoring personal activity, the method comprising: generating and sending a message to at least one user equipment, UE, if one of the following conditions is met: the server receives a signal from an electrical plug device and the received signal is in accordance with an expected pattern of signals; or the server receives a signal from an electrical plug device and the received signal is not in accordance with an expected pattern of signals; or the server does not receive a signal from an electrical plug device when a signal is expected in accordance with an expected pattern of signals.

9 Claims, 3 Drawing Sheets

(58) Field of Classification Search
USPC .................................................. 340/539.11
See application file for complete search history.

(56) References Cited

U.S. PATENT DOCUMENTS

| | | | | |
|---|---|---|---|---|
| 9,071,635 | B1* | 6/2015 | Thodupunoori | H04L 63/1416 |
| 9,503,485 | B1* | 11/2016 | Koum | H04L 65/1069 |
| 2007/0219059 | A1* | 9/2007 | Schwartz | A61B 5/0205 482/8 |
| 2008/0001735 | A1* | 1/2008 | Tran | G06F 19/3418 340/539.22 |
| 2009/0005031 | A1* | 1/2009 | Van Lieshout | H04W 36/32 455/425 |
| 2012/0056746 | A1* | 3/2012 | Kaigler | A61B 5/0022 340/573.1 |
| 2013/0049954 | A1* | 2/2013 | Scannell | H04W 68/00 340/539.11 |
| 2013/0218053 | A1* | 8/2013 | Kaiser | A61B 5/1123 600/595 |
| 2017/0003984 | A1* | 1/2017 | Gatson | G06F 9/44505 |
| 2017/0178490 | A1* | 6/2017 | Kozloski | G08B 21/0407 |

FOREIGN PATENT DOCUMENTS

| | | |
|---|---|---|
| GB | 2502062 A | 11/2013 |
| GB | 2528644 A | 2/2016 |
| WO | 2014132787 A1 | 9/2014 |

OTHER PUBLICATIONS

Intellectual Property Office of the United Kingdom (IPO) Examination Report Under §18(3) for Application No. GB1412148.7 dated Jul. 27, 2016, 1 pg.

Intellectual Property Office of the United Kingdom (IPO) Notification of Grant for Application No. GB1412148.7 dated Oct. 11, 2016, 2 pgs.

International Search Report & Written Opinion of the International Search Authority (EPO) dated Oct. 12, 2015, for International Application No. PCT/EP2015/065510, 12 pgs.

Intellectual Property Office of the United Kingdom (IPO) Combined Search & Examination Report Under §§17 & 18(3) for Application No. GB1412148.7 dated Nov. 24, 2015, 9 pgs.

Intellectual Property Office of the United Kingdom (IPO) Examination Report Under §18(3) for Application No. GB1412148.7 dated Apr. 26, 2016, 4 pgs.

* cited by examiner

ELECTRICAL PLUG DEVICE FOR MONITORING PERSONAL ACTIVITY

TECHNICAL FIELD

This invention relates to remote monitoring of behaviour of a person and more particularly, but not restricted to, remote monitoring of electrical equipment usage by a person.

BACKGROUND

People who are elderly or handicapped may be able to live independently without requiring regular care. However, it may still be desirable for relatives or friends to monitor the wellbeing of those people on a regular basis, even multiple times a day. It is not practical to visit people in need of monitoring on such a regular basis and remote monitoring is therefore desirable.

STATEMENT OF INVENTION

In accordance with a first aspect of the invention, there is provided a method of operating a server for remotely monitoring personal activity, the method comprising: generating and sending a message to at least one user equipment, UE, if one of the following conditions is met: the server receives a signal from an electrical plug device and the received signal is in accordance with an expected pattern of signals; or the server receives a signal from an electrical plug device and the received signal is not in accordance with an expected pattern of signals; or the server does not receive a signal from an electrical plug device when a signal is expected in accordance with an expected pattern of signals. The signal may be stored in a memory; and the expected pattern of signals may be estimated by a computer algorithm and is based on a plurality of stored signals. The expected pattern of signals may also be based on prior knowledge of personal activity and may be registered at the server by a user. The generated message may be sent to a plurality of UEs.

According to a second aspect of the invention, there is provided a method for remotely monitoring personal activity, the method comprising: at an electrical plug device, sending a signal to a server each time an apparatus connected to the electrical plug device is switched on or switched off; at the server, receiving the signal; establishing whether the signal is in accordance with an expected pattern of signals; generating a message if the signal is in accordance with the expected pattern of signals or if the signal is not in accordance with the expected pattern of signals, sending a message the a user equipment, UE; and at the UE, receiving the message.

At the server, the signal may be stored in a memory; and the expected pattern of signals may be estimated based on a plurality of stored signals. The expected pattern of signals may also be based on prior knowledge of the personal activity. The generated message may be sent to a plurality of UEs. The method according to the second aspect may further comprise sending a second message from one of the plurality of UEs to the server if the first message indicates that the signal is not in accordance with the expected pattern of signals, the second message indicating that the user of the UE will take an action, and sending a third message from the server to the other UEs to inform the users of the other UEs that the user will take an action.

The UE may be one of: a mobile phone, a PC, a tablet computer. The expected pattern of signals may be considered in a pre-set number of discrete time windows and the likelihood of receiving a signal in a time window may depend on behaviour in previous time windows and may be calculated with a Markov model.

According to a third aspect of the invention, there is provided a plug device comprising: means for plugging the plug device into a mains electrical socket, means for receiving a plug from an electrical apparatus, means for communicating with a server, the device being arranged to send a signal to the server if the state of the electrical apparatus changes.

The server is a mobile network server, or an internet server and the plug device may further comprise wireless communication means and/or a subscriber identification module, SIM, card. The device may further comprise an electric current analyser arranged to detect whether the electrical apparatus is switched on, switched off or on standby.

DRAWINGS

Some embodiments of the invention will now be described by way of example only and with reference to the accompanying figures, in which.

SPECIFIC DESCRIPTION

Figure 2:
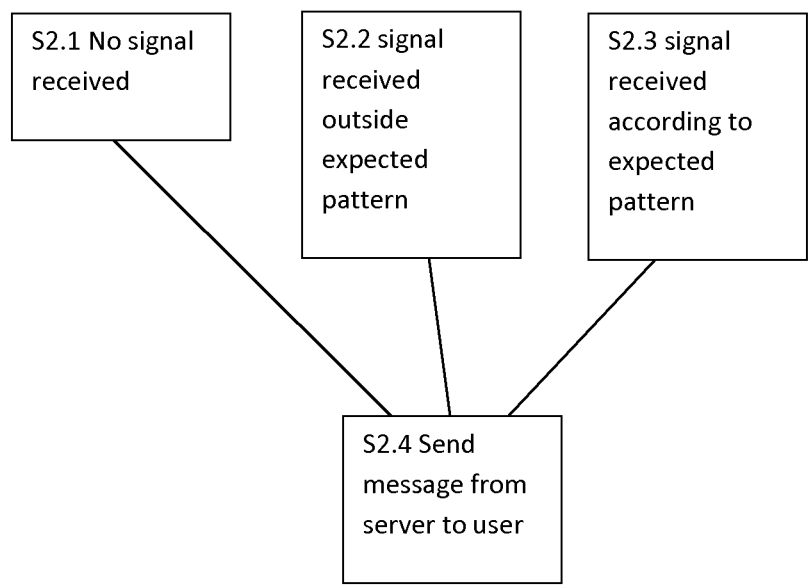
FIG. 2 is a flow diagram.
Figure 3:
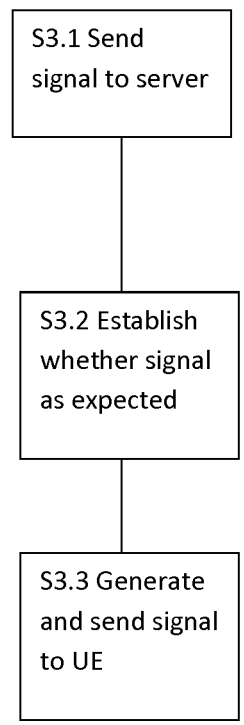
FIG. 3 is a flow diagram.

The inventors have appreciated that behaviour of people can be monitored remotely by monitoring usage of electrical equipment. The function of monitoring is arranged to be carried out in a remote server. As illustrated in FIG. 2, the function can be carried out in the server by generating and sending a message (S2.4) to a communication device of a relative or friend if one of the following conditions is met: the server receives a signal from an electrical plug device connected to the electrical equipment and the received signal is in accordance with an expected pattern of signals (S2.3); or the server receives a signal from an electrical plug device and the received signal is not in accordance with an expected pattern of signals (S2.2); or the server does not receive a signal from an electrical plug device (S2.1) when a signal is expected in accordance with an expected pattern of signals. The plug has means for plugging the plug device into a mains electrical socket, means for receiving a plug from an electrical apparatus, means for communicating with a mobile network and the device is arranged to send a signal to the mobile network if the state of the electrical apparatus changes. FIG. 3 illustrates the method of sending a signal from the plug to the server (S3.1), establishing whether the signal is as expected (S3.2) and generating and sending a signal to a user equipment (S3.3).

Expected patterns of signals, corresponding to expected patterns of behaviour, can be registered at the server by a user, for example by setting a time window within which the user expects the monitored person to change the state of the electrical apparatus during a normal day. In addition to setting the time window, the user can set an action to be carried out by the server when a signal is received inside or outside the time window, such as sending a message reporting that a signal has been received inside or outside the time window. The user thereby sets rules at the server.

Alternatively, or additionally, expected patterns of signals can be identified by an algorithm which analyses recorded signals from one person or from a group of monitored people. The patterns estimated by the algorithm can then be used to identify unusual behaviour by identifying signals which are not conform the estimated pattern. An signal which is identified as not being confirm the estimated pattern can automatically be followed up by a message sent from the server to users.

The expected pattern of signals can be set at the server by the user, or can be estimated by a computer algorithm implemented on the server. The deviation from the expected pattern can be no use when use is expected, use at abnormal times such as very early in the morning, an increase in frequency of usage such as every few minutes, slow changes of the pattern such as use at increasingly late hours of the day.

Monitoring power usage can indicate activities such making a cup of tea, watching the television and can provide a signal that a relative has woken up and is active. By monitoring activity or lack of activity, events can be communicated to the families or friends to make them aware of their loved ones status, regardless of distance.

A device such as a kettle or television is plugged into the smart plug disclosed herein and each time the kettle is turned on or off this will create a signal from the plug to a server in a cloud based service. Based upon rules set by the family or friends, the signal will activate a cascade of messages to all participating family members, for example a text message 'mum is OK' or alert them if not. The rules can be set by family members and could, for example, be to send a message 'mum is OK' to each one of the participating family members if the kettle is turned on between 9 and 11 am each morning.

All the signals from the smart plug may also be stored at the server and analysed at an individual level, but also across all active smart plugs from unrelated users to first establish patterns and then identify possible irregular trends to provide early warning systems for the family. For example, a message 'mum has started to make tea at random hours through the night' may be sent by the service if such an activity is interpreted to fall outside an established pattern.

The smart plug may appear to the user as a traditional electric plug adapter which plugs into the mains and allows an appliance such as a kettle or television to be plugged into the smart plug. Moreover, the smart plug may include a sim card in order for the plug to communicate with a mobile network without the need for a local network. Especially elderly people may not have an internet connection and a smart plug which is arranged to connect to a local wireless network may not be preferable, although that is also an option.

In a specific embodiment, the circuitry of the smart plug includes a current analyser circuit providing data of the power status of the plugged-in apparatus to be OFF, ON or in Stand-By with Stand-By being a power consumption larger than zero but less than a defined threshold. A communication circuit then takes the data from the analyser circuit and communicates the appliance status to a cloud based ecosystem. The communication circuit takes the form of a GSM Module using GPRS Data transmission to transfer the required data packets to the cloud based ecosystem. In this way, the smart plug does not require any local wifi or Internet access. However, the communication circuit could replace the GSM Module with a WiFi Module or any other Data transmission circuit to provide a data communication to and from the cloud based ecosystem.

The smart plug is arranged to send via a data connection the change of status when a power event occurs. To provide flexibility, the change of status may be reported to the server rather than just a single status. In a specific embodiment, the status values are provided as follows:

0—Starting status;
1—Power to Circuit, but no load applied from the device connected or no device connected;
2—Stand by load, i.e. the load is larger than zero but less than x, whereby x is a threshold to be defined in a specific application;
3—Power ON Load is larger than x, i.e. the device powered on.

The following table shows the transition between these status values in response to specific events:

| FROM | TO | Event |
|---|---|---|
| 0 | 1 | Plug is first switched on with no load - Normal Initial State |
| 0 | 2 | Plug Switched on with stand-by load of > 0 < x |
| 0 | 3 | Plug Switched on with load > x |
| 1 | 1 | Status Check Plug in On but no load situation returns this |
| 1 | 2 | Plug load goes from 0 to > 0 < x |
| 1 | 3 | Plug Load goes from no load to load > x ie device fully on |
| 2 | 1 | Plug load reduced to 0 from Stand by mode |
| 2 | 2 | Status check plug is in standby mode ie load > 0 < x returns these values |
| 2 | 3 | Plug load increase from Stand by to On ie from > 0 < x to > x |
| 3 | 1 | Plug goes from on to no load ie > x to 0 |
| 3 | 2 | Plug goes from on to standby ie > x to > 0 < x |
| 3 | 3 | Status Check Plug is On with Load > x returns these values |

The circuit is arranged to reset each time the plug is unplugged or disconnected from the mains supply. The circuit is arranged to send an initial status value to the server when the plug is connected to the mains supply. It is also possible that, in use, a change of status occurs during the transmission of a previous change of status and these subsequent changes of status are then buffered and sent serially.

In a specific embodiment, each communications to the server includes an IMEI Number and a MAC address if required.

The server is arranged to carry out the management of signals received from the smart plug and is arranged to send messaged to family members of friends. The criteria for when a message is sent can be set in advance, for example a message is sent if no activity between 9 am and 12 am is detected for a particular day.

The settings for sending messages and alerts may be accessed by family members through apps for smartphones and tablets or through an internet page. Messages could be sent via internet, email, SMS or via telephone calls.

A data analysis engine is provided at the server for collecting all signals from the smart plug. The signals are stored in a memory and can be used as inputs for an algorithm for pattern recognition. The algorithm is arranged to identify patterns in the behaviour of an individual user of a smart plug, but also to identify patterns in behaviour of groups of uses. Various machine learning techniques are used for behavioural tracking and identifying temporal patterns against the data of a specific individual and against the total collection of available data. These patterns will be analysed to detect possible adverse conditions, for example tea making at unusual times. When such an adverse pattern is detected then the potential issue will be communicated to the family group for their evaluation and resolution. This pattern analysis is provided in addition to the function of notifying the family members or friends when the monitored person is active or not active in a time window set by hand by the family members or friends.

The family members, which receive notifications via diverse means, such as a phone app, email, SMS, call to make them aware of their loved ones status, are arranged in a group. All members of the group may receive the same messages, or different members of the group may receive different messages depending on the nature of the message. For example, only one person may receive daily messages that all is fine with the elderly relative, while all persons in the group may receive a message if behaviour outside the normal pattern is detected. One member of the group may be responsible to selecting the settings.

When a message is sent to the whole group that an unusual pattern is detected, such as no activity within the pre-set time window, then one person needs to accept responsibility and act on the message. When one person accepts responsibility, he or she returns a message to the server to confirm this and the server is then arranged to notify the remaining members of the group that the first person has accepted responsibility and will take an action, such as call or visit the elderly relative. The responsibility cycle is a means of stopping all members of the family group panicking and all trying to contact Mum/Dad to find out what is wrong. This methodology allows individuals to accept responsibility, communicate who is taking responsibility and resolving any alerts as well as communicating the outcome in a controlled manner to all members of the group. If the responsible person has confirmed that the elderly relative is fine, then a confirmation message will be sent to the group from the server after the responsible person has indicated this to the server via the app or internet page.

Figure 1:
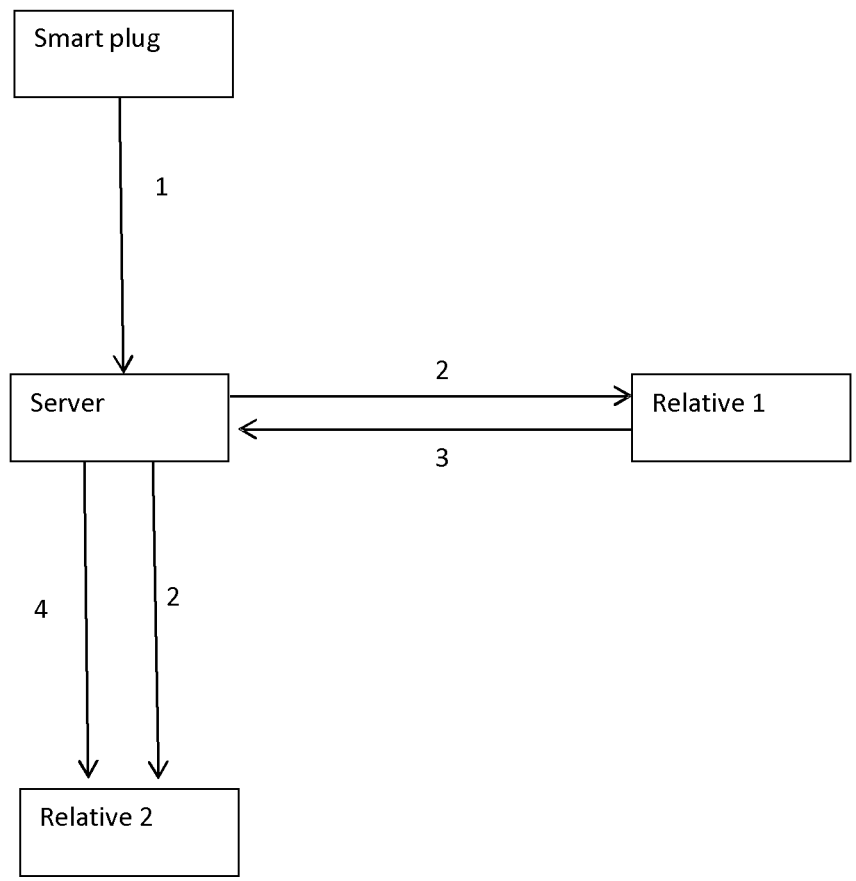
FIG. 1 illustrates a method of sending alert messages.

A specific example is illustrated in FIG. 1, which illustrates a smart plug sending a signal (1) to a server. The signal is sent at a time outside the time window in which a signal is expected according to the server. In response, the server sends a signal (2) to both relative 1 and to relative 2. Relative 2 accepts responsibility to check on the elderly relative using the smart plug and relative 2 indicates this to the server by sending a message (3). The server then sends a message (4) to relative 2 indicating that relative 1 has taken responsibility such that relative 2 knows he or she does not need to take immediate action.

A computer algorithm can be used to estimate patterns and control the distribution of messages. The data used as an input for the computer algorithm have two inputs: the power state change and the time that change takes place. In a specific embodiment, a distribution of input data across 24 discrete hours in one particular day is sufficient to distinguish periods in which usage is frequent from those in which usage is absent or not frequent. The algorithm may therefore use one-hour windows of time as a course grid. For each hour-long window the algorithm can establish a regularity metric capturing the proportion of times at least one usage was observed in this window, and the variance of the total usages in this window. These parameters in combination allow the algorithm to assign an expectation to each time window. The time windows may also be increased in size if the size of the window is too small to detect a pattern or decreased in size to improve the sensitivity.

Real time operation of the algorithm based on the grid of the pre-set time windows could be modelled as a Markov chain. The likelihood of a usage in a 'current' time window has a threshold value assigned to it based on the Markov chain and an alert can be sent by the algorithm if the threshold is exceeded.

A transition matrix for the probability $p(x_t|x_{t-1})$ describes the probability p of usage in one time window at time t conditional on usage at a previous time window at time t−1. The values of the matrix can be established with standard likelihood maximization methods for sets of daily usage, from the regularity metrics calculated previously and our domain beliefs, or a hybrid of both. In an attempt to minimise false-positives, the transition matrix can reduce the expectation in the current window if an unexpected usage in the previous window was encountered. Additionally, generation of alerts for a window could be deferred for an arbitrary period in case a usage occurred early in the following window.

A daily regularity metric can be established as a mean value of the absolute usage differences for each hour across a number of consecutive daily data sets, i.e. a mean of the hourly regularly metric mentioned above. It is then possible to observe irregular behaviour and indicate this change to a user, as well as making use of this measure at the server to influence how long we wait to hear from a device past the window of expectation before we generate an alert. The type of device may also be taken into account when analysing trends or behaviour. For example, the use of a television is likely to follow a different pattern when compared to the use of a kettle.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A method for remotely monitoring personal activity, the method comprising:
    at an electrical plug device, sending a signal to a server each time an apparatus connected to the electrical plug device is switched on or switched off;
    at the server, receiving the signal;
    establishing whether the signal is in accordance with an expected pattern of signals of at least one of a plurality of signals wherein the expected pattern of signals is based on prior knowledge of personal activity;
    generating a first message if the signal is in accordance with the expected pattern of signals or if the signal is not in accordance with the expected pattern of signals,
    sending the first message to at least one of a plurality of user equipment, UEs; and
    at the at least one of the plurality of UEs, receiving the message;
    sending a second message from a first UE of the plurality of UEs to the server if the first message indicates that the signal is not in accordance with the expected pattern of signals, the second message indicating that a user of the first UE will take an action; and
    sending a third message from the server to other UEs of the plurality of UEs to inform users of the other UEs that the user of the first UE will take an action.

2. The method of claim 1, wherein the at least one of the plurality of UEs is a mobile phone or a PC or a tablet computer.

3. The method of claim 1, wherein the expected pattern of signals is considered in a pre-set number of discrete time windows.

4. The method of claim 3, wherein the likelihood of receiving a signal in a time window depends on behavior in previous time windows and is calculated with a Markov model.

5. An assembly for remotely monitoring personal activity comprising a plug device and a server,
said plug device comprising:
  means for plugging the plug device into a mains electrical socket;
  means for receiving a plug from an electrical apparatus; and
  means for communicating with a server;
  the device being arranged to send a signal to the server if the state of the electrical apparatus changes;
said server comprising:
  means arranged to generate and send a first message from the server to at least one of a plurality of user equipment, UEs, if one of the following conditions is met:
    the server receives the signal from an electrical plug device and the received signal is in accordance with an expected pattern of signals; or
    the server receives the signal from an electrical plug device and the received signal is not in accordance with the expected pattern of signals; or
    the server does not receive the signal from an electrical plug device when a signal is expected in accordance with the expected pattern of signals,
  wherein the expected patter of signals is based on prior knowledge of personal activity and is registered at the server by a user;
  means arranged to generate and send a second message from a first UE of the plurality of UEs to the server if the first message indicates that the signal is not in accordance with the expected pattern of signals, the second message indicating that a user of the first UE will take an action; and
  means arranged to generate and send a third message from the server to other UEs of the plurality of UEs to inform users of the other UEs that the user of the first UE will take an action.

6. The plug device of claim 5, wherein the server is a mobile network server.

7. The plug device of claim 5, wherein the server is an internet server and the plug device further comprises wireless communication means.

8. The plug device of claim 6, further comprising a subscriber identification module, SIM, card.

9. The plug device of claim 5, further comprising an electric current analyzer arranged to detect whether the electrical apparatus is switched on, switched off or on standby.

* * * * *